| United States Patent [19] | [11] | 4,071,374 |
| Minton | [45] | Jan. 31, 1978 |

[54] FRICTION COSMETIC GEL

[75] Inventor: Abraham Minton, Rego Park, N.Y.

[73] Assignee: Gripsin Industries, Inc., Elizabeth, N.J.

[21] Appl. No.: 589,398

[22] Filed: June 23, 1975

[51] Int. Cl.$^2$ .............................. C08L 1/08; C09J 3/04
[52] U.S. Cl. .................................. 106/189; 106/193 J; 106/197 R; 106/203; 106/204; 252/316; 252/317; 424/357; 424/362
[58] Field of Search .................... 106/193, 189, 36; 424/362, 357; 252/317, 316

[56] References Cited

U.S. PATENT DOCUMENTS

| 2,441,422 | 5/1948 | Krieble | 252/316 |
| 2,678,902 | 5/1954 | Mehaffey | 424/362 |
| 3,415,939 | 12/1968 | Minton | 424/357 |
| 3,636,200 | 1/1972 | Zentner | 424/357 |
| 3,738,957 | 6/1973 | Iler | 252/316 |
| 3,895,956 | 6/1975 | Yoshida | 106/287 S |
| 3,899,439 | 8/1975 | Mahlman | 252/316 |

*Primary Examiner*—Theodore Morris
*Attorney, Agent, or Firm*—Lerner, David, Littenberg & Samuel

[57] ABSTRACT

A grip-improving gel, primarily for application to the skin, is disclosed. The gel includes a fine particle size silica, a compatible gelling agent for improving the adherence of the gel to the skin, and an aqueous solution of a $C_1$ to $C_4$ alcohol. In a highly preferred embodiment, the gelling agent comprises an organoclay compound or an organic derivative of a hydrous magnesium and/or aluminum silicate, and the fine particle size silica is hydrophobic, preferably being prepared by the reaction of a fumed silica with a silane.

14 Claims, No Drawings

FRICTION COSMETIC GEL

FIELD OF THE INVENTION

The present invention relates to grip-improving gels, primarily for application to the skin. More specifically, the present invention relates to cosmetic gells which, upon drying, leave a thin, strongly adherent, dry film thereon. Still more specifically, the present invention relates to cosmetic gels for application to the hands, to aid in improving the grip, particularly for use in athletic activities. Furthermore, the present invention also relates to such grip-improving gels for application to objects to be handled, such as by athletes, in order to improve their grip thereof.

BACKGROUND OF THE INVENTION

In the past, many cosmetic preparations have been employed in order to aid in improving ones grip, particularly during athletic competition. Thus, in order to improve the hand grip for athletes, particularly in sports such as tennis, bowling, golf, baseball, rowing, etc., two basic types of preparations have been employed. On the one hand, various powders, such as rosin powder, have been employed. The various talcs and rosin powders, however, can only achieve temporary assistance in improving the grip, since they rub off rather easily, do not adhere to the skin surface, and thus require constant and frequent reapplication in order to be of any assistance at all. In addition, these powders are quite messy, easily soil clothing, etc.

On the other hand, various tacky ointments or ointment mixtures have been employed for such purposes. These ointments generally have pressure sensitive properties, which tend to make skin quite tacky, and readily adhere to all surfaces with which they come in contact. For this reason, aside from the obvious interference of such compounds in ones normal activities, even in the sports or other activities for which they are intended, they have not proven successful. This is particularly so in sports such as baseball or bowling where it is necessary to maintain a good grip, but also to maintain a quick release. When tacky ointments or pine tars are employed for such purposes the tackiness inherently results in inability to obtain such quick release therewith.

It has also been taught in the past to prepare certain cosmetic preparations for application to the skin which impart a durable matte appearance thereon, particularly to eliminate shiney surfaces thereon. Thus, in U.S. Pat. No. 3,415,939, issued on Dec. 10, 1968, such preparations are disclosed and include the following ingredients (a) lower alkyl alcohols, (b) higher fatty alcohols, (c) metal salts of n-alkyl sulfates, and (d) hydrophillic colloidal hydrous aluminum silicates. These compositions have proven to be capable of applying such matte finishes, but are not intended, nor can they in any way accomplish the application of thin strongly adhering dry films to the skin for improving ones grip. The search for such compounds, particularly of the type which can be widely used commercially, has therefore continued.

SUMMARY OF THE INVENTION

According to the present invention, it has now been discovered that gels can be prepared, primarily for application to the skin, by combining the following principal ingredients:

1. A fine particle size silica:
2. A minor amount of a compatible gelling agent for improving the adherence of the gel to the skin or other surface to which it is applied; and
3. A major amount of an aqueous solution of a $C_1$ to $C_4$ alcohol, so that upon the application of such a gel to the skin or other surface a think, non-tacky, strongly adhering dry film is formed thereon.

In a preferred embodiment of the present invention, the compatible gelling agent employed is selected from the group consisting of organoclay compounds, particularly of hydrous magnesium silicates, and organic derivatives of the hydrous magnesium and/or aluminum silicates, preferably containing adsorbed exchangeable non-toxic, non-irritant hydrophillic organic cations, particularly alkyl-ammonium, hydroxy-alkyl ammonium, and quaternary ammonium cations.

It is also highly preferred that the fine particle size silica be hydrophobic, and it is preferably a hydrophobic silica formed from the reaction of a fumed silica with a silane, preferably a silane having the formula $SiR_nX_{4-n}$, wherein R comprises a lower alkyl, such as a $C_1$ through $C_3$ alkyl, and most preferably a methyl group, and X comprises a halogen, preferably chlorine, so that $n$ is therefore an integer from 1 to 3, preferably 2 or 3.

It is preferred that the aqueous solution of a $C_1$ through $C_4$ alcohol comprise an alcohol selected from the group consisting of methanol, ethanol, isopropanol and propanol.

In another embodiment of the present invention the above-described cosmetic gel will also include various fragrances and/or pigments which add to the cosmetic acceptability of the gel.

DETAILED DESCRIPTION

Basically, the present invention provides for the preparation and application of a thin layer of a fumed silicone dioxide-containing gel, preferably to the skin, particularly the hands. The silicone dioxide (silica) employed in the present invention thus comprises an extremely fine particle size silica, i.e., having an average particle size of between about 7 and 40 mu in diameter. Such a fine particle size silica may be prepared by the flame decomposition of silicone tetrachloride, producing such a fumed silicone dioxide, which is hydrophillic in nature, particularly due to the fact that it has about 0.5 millimoles of silanol groups in each hundred square meters of surface area.

It has been found that the application of such fumed silicone dioxide to the skin provides what has been termed a state of superfriction. That is, the rubbing together of skin to which such a coating has been applied produces a dramatic increase in friction as compared to such skin before the application of any such coating. Three specific commercially available grades of extremely fine particle size hydrophillic silicas are products of the Cabot Corporation, CAB-O-SIL, and of Degussa, AEROSIL. It has been found, however, that the use of modified fumed silicas which are hydrophobic in nature is highly preferred in the cosmetic gels of the present invention. Specifically, such silicas wherein at least a portion of the silanol groups on the surface thereof have been replaced with various organic radicals are extremely useful in the gels of the present invention. Thus, the attachment of hydrophobic hydrocarbon groups for at least a portion of the hydroxyl groups on the surface of such silicas produces a highly hydrophobic product. Examples of commercially available grades of said hydrophobic silicas (fumed silicon dioxides) are AEROSIL R-972, (in which dimethyl groups are so substituted) a product of Degussa, and TULLANOX 500 (previously sold under the name SILANOX 101) (in which trimethyl groups are so substituted) a product of Tulco, Inc. Such hydrophobic fumed silicas in the gels of the present invention are capable of imparting water repellancy to the film adhered to the skin, and the film tends to remain dry in spite of perspiration produced by physical exertion and/or hot humid weather. Preferably, such hydrophobic silicas are prepared by the reaction of silicone dioxide with a silane. Preferably, a silane having the general formula as follows is employed;

$SiR_nX_{4-n}$, wherein R is lower alkyl, preferably methyl, X is a halogen, preferably chlorine, and $n$ is an integer from 1 to 3, preferably 2 or 3. In a most preferred embodiment, the silane with which the silicone dioxide is reacted comprises dimethyl-dichlorosilane or trimethyl-chlorosilane.

In order to prepare a suitable preparation for the gel of the present invention an alcohol is employed to wet out the silica. Preferably a $C_1$ through $C_4$ alcohol is employed, most preferably lower alcohols, such as ethanol, isopropanol, and/or propanol are employed. Most preferably, isopropanol or ethanol are employed. While methanol, due to its toxic nature when applied to the skin, will normally not be used in preparing the cosmetic gels of this invention, it could be employed in such grip-improving gels which are to be applied directly to athletic equipment and the like which is to be gripped, such as tennis rackets, baseball bats, golf clubs, bowling balls, etc. Furthermore, while $C_4$ and higher alcohols, such as butanol, secondary butanol, tertiary butanol and isobutanol can be utilized, they will generally not be preferred due to their reduced solubilities in water and their generally objectionable odors.

The use of such alcohols not only allows the silicas of this invention, primarily the hydrophobic silicas, to be wet out during preparation of the gels, as well as prepare the silica for application to the skin, but it also allows the final preparation to dry rapidly when applied, and as a thin film or layer, either on one's skin or on the item to which it is applied.

The alcohol itself is used in an aqueous solution, generally comprising between about 12 and 65% alcohol by weight, preferably about 57% by weight.

In order to provide for a strongly adherent coating of the gels of the present invention a compatible gelling agent is employed. Such gelling agents may thus include various cellulose gums, including natural gums, etc., however, the use of various hydrophillic colloidal hydrous magnesium and/or aluminum silicates is preferred. These hydrophillic colloidal hydrous magnesium or aluminum silicates are generally characterized by the property of further hydrating and swelling in water and ultimately forming a slurry or gel. Illustrative of the colloidal hydrous aluminum silicates are the montmorillonite clays such as bentonite or treated bentonites, and an example of a colloidal hydrous magnesium silicate is hectorite. These hydrophillic colloidal magnesium and/or aluminum silicates may also contain adsorbed exchangeable metal cations, particularly alkali and alkaline earth metal cations, and may also preferably contain adsorbed exchangeable non-toxic, non-irritant hydrophillic organic cations, particularly alkylammonium, hydroxy-alkyl ammonium, as for example, the tris (hydroxy ethyl) methyl ammonium cation and quarternary ammonium cations. It is also highly preferred, however, that organoclay compounds or mixtures be employed, such as a mixture of a compatible organic compound and hydrous magnesium silicates. In particular, an organic suspending agent, such as hydroxyethyl cellulose, or other such cellulosic compounds, are preferred.

One commercially available colloidal magnesium aluminum silicate containing adsorbed exchangeable alkali metal and alkali earth metal cations is sold under the trademark "VEEGUM." A commercially available colloidal magnesium silicate containing adsorbed exchangeable hydroxy alkyl ammonium cations is sold under the trademark "VEEGUM-PRO." VEEGUM is a standard item of commerce and is sold under the tradename by the R. T. Vanderbuilt Company, Inc., and its preparation is described in U.S. Pat. No. 2,523,204. The chemical analysis of VEEGUM, as expressed in terms of oxide, is as follows:

Silicone Dioxide: 61.1
Magnesium: 13.7
Aluminum Oxide: 9.3
Titanium Dioxide: 0.1
Ferric Oxide: 0.9
Calcium Oxide: 2.7
Sodium Oxide: 2.9
Potassium Oxide: 0.3
Carbon Dioxide: 1.8
Water of Combination: 7.2

VEEGUM-PRO is also a standard item of commerce marketed by the R. T. Vanderbuilt Company, Inc., but differs from the other grade of VEEGUM in that it contains tris (hydroxy ethyl) methyl ammonium cations.

A more highly preferred hydrous magnesium silicate, however, is marketed under the tradename BENTONE LT, and sold under that name by N. L. Industries, Inc. This material is an organoclay, that is a mixture of a compatible organic compound, in this case hydroxy ethyl cellulose, and a hydrous magnesium silicate, hectorite. The BENTONE LT, which is a staple article of commerce, has thus been found to be particularly effective in the gels of this invention.

In the gel compositions of the present invention, the overall gel will generally comprise from about 3 to about 10 weight percent of the fine particle size silica, preferably more than about 3 weight percent, more preferably more than about 6 weight percent and most preferably between about 6 and 10 weight percent. On the other hand, the alcohol will generally comprise between about 12 and 65 weight percent of the final gel, and preferably from about 45 to about 57 weight percent. Finally, the compatible gelling agent will generally comprise from about 0.5 weight percent up to about 2 weight percent or more of the final product, depending upon the viscosity of the gel which is desired. Preferably from about 1 to 1.5 weight percent of the gelling agent will be employed. This will also depend upon the particular method of application desired, such as whether a flowable gel is desired, or a much thicker gel for use in application from flexible plastic bottles, etc. The cosmetic gel of the present invention will generally be prepared by first preparing the aqueous solution of the alcohol to be employed, and with continuous vigorous stirring, adding the compatible gelling agent, such as the hydrous colloidal magnesium and/or aluminum silicate thereto, continuing the stirring, preferably until there is no additional rise in the viscosity of the gel thus formed. Subsequently, the silica may be added in small portions, with continuous stirring, until it is dispersed throughout the gel, and again the viscosity of the gel remains substantially constant. The form of silica employed, preferably a hydrophobic silica, is preferably applied to a vortex formed in the stirred gel, for easier dispersion.

In a preferred method of preparation, however, approximately one-half of the amount of the alcohol to be employed in the aqueous alcohol solution is maintained in a stirred condition, and the compatible gelling agent is added thereto, forming a mere suspension. With added stirring, the total amount of required water may then be added to the stirred suspension, and hydration will then begin immediately and reach a maximum much sooner. When this maximum has been reached, as evidenced by the viscosity remaining substantially constant, the balance of the alcohol may then be added. The final gel preparation may then continue as above, namely by the addition of small portions of the silica thereto with continuous stirring in order to maintain the fine dispersion of the present invention.

Product consistency may also be effected by the extent and duration of agitation, as well as by the nature of the hydrous aluminum silicate employed.

In order to made these compositions cosmetically acceptable, various compatible perfumes may be incorporated thereinto in addition to various dyes and/or pigments in order to simulate skin tones. Any perfume concentrate having a pleasant fragrance, such as bouquets that simulate the various flowers, may be employed. Also, the so-called specialty perfumes sold under various tradenames, may also be utilized. For example, there are the so-called UNISEX fragrances that are designed to be simultaneously suitable for both sexes. In addition, individual oils like lemon, mint, orange, lime, cinnamon, sassafras, clove, etc. may be used. The use of about 0.05% to 0.25% of the total gel will normally be sufficient. The fragrance must, however, be soluble in alcohol.

As for the dyes that may be utilized, all of the F. D. & C. (Food, Drug and Cosmetics) certified dyes may be used. In addition iron oxide pigment may be suspended in the gel to simulate the various skin tones if desired. These tones can be obtained by blending together yellow, red and brown iron oxide cosmetic pigments, in various proportions. The total percentage of these iron oxides will thus generally vary from about 0.0%, to obtain a tint in the gel, to about 3% to get a tint in the dried film.

There are also some D & C certified pigments that are deep red, blue, violet, etc. which can also be judicially used.

EXAMPLE 1

(Parts by weight for 100 pounds)

Twenty-seven pounds of isopropyl alcohol were added to a suitable tank equipped with a variable speed propeller-type stirrer. The stirrer was started, and then 1.25 pounds of BENTONE LT was added to the vortex formed therein. Subsequently, the 0.1 pounds of a unisex perfume was added to the tank, and then 39.65 pounds of water was very rapidly added thereto. After about five minutes of stirring, the speed of the stirrer was increased, and then the vigorous stirring was continued for 30 minutes to complete the hydration of the BENTONE LT. The speed of the propeller was then increased to a maximum, and the remaining 26 pounds of isopropyl alcohol was added slowly into the vortex formed therein. Finally, 6 pounds of AEROSIL R972 was added in small increments into the vortex, and stirring was continued for about 10 to 20 minutes after the last increment of the AEROSIL R972 was added. In this example, 57.2% isopropyl alcohol be weight was contained in the alcohol water solution utilized.

EXAMPLE 2

(Parts by weight for 100 pounds)

In this example, 50 pounds of ethyl alcohol (190 proof) were added to a suitable size tank equipped with a variable speed stirrer, and the stirrer was started at medium speed (stirring was continued until the conclusion of the entire run). 41 pounds of water were added to the tank, and shortly thereafter the stirring speed was increased, and 3 pounds of VEEGUM HV was quickly sprinkled into the vortex formed in the tank. After about 10 minutes, AEROSIL R972 was added into the vortex in increments, up to a total of 6 pounds thereof. The stirring was continued for about an hour more, until the maximum viscosity was reached, at which point the perfumes were added.

EXAMPLE 3

(Parts by weight for 100 pounds)

A subsequent sample of the gel of the present invention can be prepared in propyl alcohol. Thus, in a suitable tank equipped with a variable speed propeller type stirrer, 35 pounds of propyl alcohol and 56 pounds of water is added, and stirring is commenced. Speed is adjusted to get a suitable vortex in the tank, and 2.4 pounds of VEEGUM PRO is quickly added thereto. The speed is increased whenever necessary in order to maintain a vortex, and after 30 minutes 6.5 pounds of AEROSIL R972 is added in increments. Stirring is continued for about 30 minutes after the last increment of AEROSIL R972 is added, and the maximum speed is employed for the final stage, at which point the perfumes may be added.

EXAMPLE 4

(Parts by weight for 100 pounds)

In this example, a grip-improving gel of the present invention was prepared employing TULLANOX as a source of silica. In a procedure similar to those described in Examples 1, 2 and 3 52.3 pounds of isopropyl alcohol is charged into a suitable tank, again as described in Example 3. 39.1 pounds of water is then added, and then the following iron oxides are then added thereto:

0.5 pounds of red iron oxide, 0.5 pounds of yellow iron oxide, and 1.0 pounds of brown iron oxide, with stirring during this entire period. The speed of the stirrer is then increased to a maximum, and an entire 1.5 pounds of BENTONE LT is then added to the tank as quickly as possible, in order to avoid lumps. Stirring is continued for about 30 minutes and then 5.0 pounds of TULLANOX is added in increments, until the entire 5 pounds has been so added. Stirring is then continued, and a gel which has a skintone color in the film on application to the skin, after drying, has been prepared.

What is claimed is:

1. A grip-improving gel which comprises a fine particle size hydrophobic silica, said hydrophobic silica being formed from a reaction of silica with a silane, said silane having the general formula of $SiR_nX_{4-n}$, wherein R comprises a lower alkyl, X comprises a halogen, and n is from 1 to 3, a minor amount of a compatible gelling agent for improving the adherence of said gel, said compatible gelling agent being selected from the group consisting of cellulose gums, hydrous magnesium and aluminum silicates, organic derivatives of the hydrous magnesium and the aluminum silicates, and mixtures thereof, and a major amount of an aqueous solution of a $C_1$ through $C_4$ alcohol, so that upon the application of said gel a thin, non-tacky, strongly adhering dry film is formed.

2. The grip-improving gel of claim 1 wherein said hydrophobic silica is formed from a reaction of silica with a silane.

3. The grip-improving gel of claim 1 wherein said lower alkyl comprises a $C_1$ through $C_3$ hydrocarbon.

4. The grip-improving gel of claim 3 wherein said lower alkyl comprises methyl.

5. The grip-improving gel of claim 1 wherein said halogen comprises chlorine.

6. The grip-improving gel of claim 2 wherein said silane is selected from the group consisting of dimethyl-dichlorosilane, trimethyl-chlorosilane and mixtures thereof.

7. The grip-improving gel of claim 1 wherein said compatible gelling agent comprises a hydrous magnesium silicate in admixture with a cellulosic compound.

8. The grip-improving gel of claim 7 wherein said cellulosic compound comprises hydroxy ethyl cellulose.

9. The grip-improving gel of claim 1 wherein said organic derivative comprises an adsorbed hydrophillic organic cation selected from the group consisting of alkyl ammonium, hydroxy alkyl ammonium, and quaternary ammonium cation.

10. The grip-improving gel of claim 1 wherein said alcohol is selected from the group consisting of methyl, ethyl, iropropyl and propyl alcohol.

11. The grip-improving gel of claim 1 wherein said aqueous solution of said $C_1$ through $C_4$ alcohol comprises between about 12 and 65 weight percent alcohol.

12. The grip-improving gel of claim 11 including from about 12 to about 65 weight percent of said $C_1$ through $C_4$ alcohol.

13. The grip-improving gel of claim 1 including from about 0.5 to about 2 weight percent of said compatible gelling agent.

14. The grip-improving gel of claim 1 including between about 6 and 10 weight percent of said hydrophobic silica.

* * * * *

UNITED STATES PATENT AND TRADEMARK OFFICE
CERTIFICATE OF CORRECTION

PATENT NO. : 4,071,374
DATED : Jan. 31, 1978
INVENTOR(S) : Abraham Minton

It is certified that error appears in the above-identified patent and that said Letters Patent are hereby corrected as shown below:

Column 5, line 48, "0.0%" should read --0.1%--.

Signed and Sealed this

First Day of August 1978

[SEAL]

Attest:

RUTH C. MASON
Attesting Officer

DONALD W. BANNER
Commissioner of Patents and Trademarks